US006680071B1

(12) United States Patent
Johnson et al.

(10) Patent No.: US 6,680,071 B1
(45) Date of Patent: Jan. 20, 2004

(54) OPIOID AGONIST IN A FAST DISPERSING DOSAGE FORM

(75) Inventors: Edward Stewart Johnson, Ruscombe (GB); Jon Lacy, Genthod (CH)

(73) Assignee: R. P. Scherer Technologies, Inc., Paradise Valley, NV (US)

( * ) Notice: Subject to any disclaimer, the term of this patent is extended or adjusted under 35 U.S.C. 154(b) by 0 days.

(21) Appl. No.: 09/936,060

(22) PCT Filed: Mar. 2, 2000

(86) PCT No.: PCT/US00/05531

§ 371 (c)(1),
(2), (4) Date: Jan. 14, 2002

(87) PCT Pub. No.: WO00/51539

PCT Pub. Date: Sep. 8, 2000

(30) Foreign Application Priority Data

Mar. 3, 1999 (GB) ................................................ 9904911

(51) Int. Cl.$^7$ .......................... A61K 9/14; A61K 47/00
(52) U.S. Cl. ...................... 424/484; 424/485; 424/486; 424/487; 424/488; 424/439; 424/441; 424/465; 424/466; 514/329; 514/816; 514/817; 514/818
(58) Field of Search ................................. 424/484, 485, 424/486, 487, 488, 439, 441, 465, 466; 514/329, 816, 817, 818

(56) References Cited

U.S. PATENT DOCUMENTS

| 4,371,516 A | * | 2/1983 | Gregory et al. ................ 424/22 |
| 4,855,326 A | | 8/1989 | Fuisz .......................... 514/777 |
| 5,079,018 A | | 1/1992 | Ecanow ....................... 426/385 |
| 5,112,616 A | * | 5/1992 | McCarty ....................... 424/435 |
| 5,298,261 A | | 3/1994 | Pebley et al. ................. 424/488 |
| 6,495,120 B2 | * | 12/2002 | McCoy et al. ................. 424/45 |

FOREIGN PATENT DOCUMENTS

| EP | 0 627 218 A1 | 12/1994 |
| WO | WO 91/04757 | 4/1991 |
| WO | WO 93/12769 | 7/1993 |
| WO | WO 94/14422 | 7/1994 |

OTHER PUBLICATIONS

US 5,120,549, 6/1992, Gole et al. (withdrawn)
Stanley et al. entitled: "Oral Transmucosal Fentanyl Citrate (Lollipop) Premedication in Human Volunteers", *Anesth. Analg.*, Jan. 1989, 69(1), pp. 21–27.
Portenoy et al. entitled: "Oral transmucosal fentanyl citrate (OTFC) for the treatment of breakthrough pain in cancer patients: a controlled dose titration study", abstract, *Pain*, Mar., 1999, 79(2,3), pp. 303–312.

* cited by examiner

*Primary Examiner*—Frederick Krass
(74) *Attorney, Agent, or Firm*—Donald O. Nickey

(57) ABSTRACT

This invention relates to a pharmaceutical composition for oral administration comprising a carrier and, as active ingredient, an opioid (μreceptor) agonist, such as fentanyl, or a salt thereof, characterized in that the composition is in the form of a fast-dispersing dosage form designed to release the active ingredient rapidly in the oral cavity. A process for preparing such a composition and the use of such a composition as an analgesic, for the treatment of chronic pain and/or breakthrough pain, as an anesthetic premedication, for the induction of anesthesia, as a sedative and/or for the treatment of anxiety are also provided.

12 Claims, No Drawings

OPIOID AGONIST IN A FAST DISPERSING DOSAGE FORM

RELATED APPLICATIONS

This application is a national phase filing under 35 U.S.C. 371 of International Application No. PCT/US00/05531 (WO 00/51539) filed Mar. 2, 2000, which claims the benefit of priority to Great Britain Application No. 9904911.6 filed Mar. 3, 1999.

TECHNICAL FIELD

This invention relates to a pharmaceutical composition in the form of a fast dispersing dosage form and to a process for preparing such a composition. The invention also relates to the use of such a composition as an analgesic for the treatment of chronic pain and/or breakthrough pain, as an anesthetic premedication for the induction of anesthesia as a sedative and as a treatment for anxiety.

BACKGROUND OF THE INVENTION

Fentanyl (N-phenyl-N-[1-(2-phenylethyl)-4-piperidinyl] propanamide) is a potent synthetic opioid ($\mu$ receptor) agonist, related to pethidine, which possesses a fast onset and a moderate duration of action. The agonists useful in the present invention are chemical substances capable of combining with a receptor on a cell and initiating a reaction or activity that is characteristics of opiate narcotics, but which is not derived from opium.

Fentanyl, like other opioid agonists, interacts predominantly with $\mu$ binding sites in the brain, spinal cord and other tissues. Its principal pharmacological actions of therapeutic value are analgesia and sedation and, in this respect, fentanyl is approximately 100 times more potent than morphine and 7,500 times more potent than pethidine. It is therefore primarily used for its analgesic properties as a component of anesthesia and is normally administered by intravenous or intramuscular injection, although transdermal and transmucosal dosage forms have also been developed.

When administered by the intravenous route, the onset of activity is almost immediate and the duration of analgesia is about 30 to 60 minutes after a single dose of up to 0.1 mg. Following intramuscular administration of fentanyl, the onset of activity is 7 to 8 minutes with a duration of activity of 1 to 2 hours. Intravenous fentanyl may therefore be utilized for analgesic action of short duration during the anesthetic periods of premedication, induction and maintenance and in the immediate postoperative period (recovery room) as the need arises. It may also be used as a narcotic analgesic supplement in general or regional anesthesia and, with a neuroleptic agent such as droperidol, as an anesthetic premedication for the induction of anesthesia and as an adjunct in the maintenance of general and regional anesthesia. In selected high risk patients, such as those undergoing open heart surgery or certain complicated neurological or orthopaedic procedures, it may also be used as an anesthetic agent with oxygen.

Typical dosages for use as a premedication or postoperatively are 50 to 100 $\mu$g/kg of body weight. When used as an adjunct to general anesthesia, doses may range from 2 $\mu$g/kg to 20–50 $\mu$g/kg depending upon the complexity and duration of the operation.

Intravenously administered fentanyl tends to accumulate in skeletal muscle and fat from where it is slowly released into the blood. Repeated doses therefore lead to accumulation and prolonged activity. The plasma protein binding decreases with increasing ionization of the drug and alterations in pH may therefore affect the distribution of fentanyl between plasma and the central nervous system. Fentanyl is primarily transformed in the liver and a high first pass effect is therefore observed when the drug is administered by non-parenteral routes. However, about 75% of an intravenous dose of fentanyl is recovered in the urine with less than 10% as the unchanged drug, the main metabolites being norfentanyl and despropionylfentanyl which are both inactive.

In addition to analgesia, fentanyl may cause alterations in mood, euphoria, dysphoria and drowsiness. Moreover, therapeutic levels of fentanyl may cause nausea and vomiting directly by stimulation of the chemoreceptor trigger zone. However, nausea and vomiting are significantly more common in ambulatory than in recumbent patients.

One of the most serious adverse effects associated with use of intravenous fentanyl is hypoventilation. This is seen as a reduction in the respiratory rate (breaths per minute) and in the oxygen saturation level of the blood. Indeed, this hypoventilation may last longer than the analgesic effect. It is therefore necessary to ensure that an opioid antagonist, intubation equipment and oxygen are readily available when fentanyl is injected.

Fentanyl may also cause muscle rigidity, particularly in the muscles of respiration. This may occur in the postoperative period and patients should therefore be carefully monitored, especially those receiving a high dose of fentanyl. Should this effect occur, it may be reversed by administration of naloxone or overcome by neuromuscular-blocking drugs.

As with other opioid agonists, fentanyl increases the tone and decreases the propulsive contractions of the gastrointestinal tract leading to constipation. However, at therapeutic dosages, fentanyl exerts minimal effects on the cardiovascular system, although orthostatic hypotension and fainting may occur in some patients and vagally-mediated bradycardia has been reported.

The transdermal dosage form is available as a range of patches offering a range of release rates from 25 to 100 $\mu$g of fentanyl per hour over 3 days. In this dosage form, fentanyl is released as a free base. The actual amount released from the patch varies with time and also between patients. Essentially, the skin absorbs fentanyl and a depot of fentanyl concentrates in the upper skin layers. The serum fentanyl concentrations gradually increase until levelling off with peak serum concentrations being attained between 24 and 72 hours. After several sequential 72-hour applications, patients reach and maintain a steady state serum concentration. After removal of the patch, the serum fentanyl concentrations gradually decline with levels falling by 50% in about 17 hours. This slower elimination, as compared to that after intravenous administration, is due to continued absorption of drug from the depot in the skin after removal of the patch.

In view of the above, the transdermal patch is indicated for the management of chronic pain in patients who require continuous opioid analgesia for pain that cannot be managed by paracetamol-opioid combinations, non-steroidal analgesics or PRN dosing with short acting opioids. It is not indicated for the management of acute or postoperative pain because of the risk of hypoventilation (4% incidence) and should not be administered to children under 12 unless used in an authorized research setting.

The oral transmucosal system consists of a lozenge of fentanyl citrate attached to a handle. The lozenge is sucked until complete dissolution is achieved (normally within about 12 to 15 minutes). A bioavailability study of this device in comparison with intravenous and oral solution administration showed that the absolute bioavailability from the device was 51%, as compared to 32% from the oral solution, and that the $t_{max}$ was also faster from the device. It is estimated that about 75% of the total dose from the device is swallowed and a third of this amount reaches the systemic circulation in addition to the 25% of the dose which is absorbed sublingually.

The oral transmucosal device has been approved for use for anesthetic premedication in children and adults and for use in anesthesia or monitored anesthesia care. The approved dose for this dosage form for premedication is between 5–15 μg/kg (400 μg) for adults. However, this product is only authorized for administration in hospital settings where there is immediate access to life support equipment, including oxygen, facilities for endotracheal intubation, intravenous fluids and opioid antagonists. Also, there is a restriction on personnel authorized to administer this product.

This device is clearly unsuitable for use during and after operations and can therefore only be used for some of the indications for which the intravenous injection form can be used. Also, although several clinical trials have shown that the oral transmucosal device is generally useful as a premedicant in children prior to surgery, there is a high incidence of adverse effects, some of which could complicate the induction of anesthesia.

The main adverse effect is mild facial pruritus (incidence of about 50 to 60%) but the occurrence of nausea and vomiting has also been high (30 to 50%). Indeed, the high incidence of vomiting in one study in children led to the termination of the study and is probably the most troublesome side-effect. Moreover, pre-treatment with an antiemetic has not proved to be effective in decreasing the incidence of nausea and vomiting. In addition, the device has also been shown to reduce oxygen saturation levels in blood in some children, thus necessitating constant blood oxygen monitoring in patients taking the product. There are thus significant drawbacks with respect to the adverse event profile which may limit the clinical usefulness of the oral transmucosal device form of fentanyl in some settings as a premedication before surgery.

Approval has been sought for the use of the transmucosal device in the treatment of breakthrough pain in chronic pain patients already receiving opioid therapy in home or hospital settings. The regulatory authorities have expressed concern regarding the incorporation of a potent and narcotic drug into a device, which looks like a child's confectionery product. It is feared that the lollipop form of the product would be attractive to a child, and result in accidental consumption of the narcotic, with potential life-threatening consequences.

It is clear from the above that it would be highly desirable from a clinical point of view to find a way of administering fentanyl and other opioid (μ receptor) agonists which is easy for the patient to accomplish and which bypasses first pass metabolism in the liver while still providing good bioavailability of the active ingredient and a rapid onset of activity.

According to the present invention there is therefore provided a pharmaceutical composition for oral administration comprising a carrier and, as active ingredient, an opioid (μ receptor) agonist, characterized in that the composition is in the form of a fast-dispersing dosage form designed to release the active ingredient rapidly in the oral cavity.

It has been found that such fast-dispersing dosage forms promote pre-gastric absorption of the active ingredient, that is, absorption of the active ingredient from that part of the alimentary canal prior to the stomach. The term "pre-gastric absorption" thus includes buccal, sublingual, oropharyngeal and oesophageal absorption. An opioid (μ receptor) agonist, such as fentanyl, absorbed by such pre-gastric absorption, passes straight into the systemic circulatory system thereby avoiding first pass metabolism in the liver. Accordingly, bioavailability of an opioid (μ receptor) agonist, such as fentanyl, absorbed in this way may also be increased. This means that the dose of fentanyl or other opioid (μ receptor) agonist may be reduced while still producing the desired beneficial effects and this decrease in dose will result in a corresponding reduction of unwanted side effects.

One example of a fast-dispersing dosage form is described in U.S. Pat. No. 4,855,326 in which a melt spinnable carrier agent, such as sugar, is combined with an active ingredient and the resulting mixture spun into a "candy-floss" preparation. The spun "candy-floss" product is then compressed into a rapidly dispersing, highly porous solid dosage form.

U.S. Pat. No. 5,120,549 discloses a fast-dispersing matrix system which is prepared by first solidifying a matrix-forming system dispersed in a first solvent and subsequently contacting the solidified matrix with a second solvent that is substantially miscible with the first solvent at a temperature lower than the solidification point of the first solvent, the matrix-forming elements and active ingredient being substantially insoluble in the second solvent, whereby the first solvent is substantially removed resulting in a fast-dispersing matrix.

U.S. Pat. No. 5,079,018 discloses a fast-dispersing dosage form which comprises a porous skeletal structure of a water soluble, hydratable gel or foam forming material that has been hydrated with water, rigidified in the hydrated state with a rigidifying agent and dehydrated with a liquid organic solvent at a temperature of about 0° C. or below to leave spaces in place of hydration liquid.

Published International Application No. WO 93/12769 (PCT/JP93/01631) describes fast-dispersing dosage forms of very low density formed by gelling, with agar, aqueous systems containing the matrix-forming elements and active ingredient, and then removing water by forced air or vacuum drying.

U.S. Pat. No. 5,298,261 discloses fast-dispersing dosage forms which comprise a partially collapsed matrix network that has been vacuum-dried above the collapse temperature of the matrix. However, the matrix is preferably at least partially dried below the equilibrium freezing point of the matrix.

Published International Application No. WO 91/04757 (PCT/US90/05206) discloses fast-dispersing dosage forms which contain an effervescent disintegration agent designed to effervesce on contact with saliva to provide rapid disintegration of the dosage form and dispersion of the active ingredient in the oral cavity.

EP-A-0627218 discloses a fast-dispersing dosage form which comprises a tablet comprising a sugar alcohol or the like as principal ingredient which is prepared by the wet granulation method in which a kneaded mixture of the sugar alcohol or the like with a drug is compression molded before drying.

Published International Application No. WO 94/14422 describes a process for drying frozen discrete units in which the solvent is removed under conditions whereby the solvent is evaporated from the solid through the liquid phase to a gas, rather than subliming from a solid to a gas as in lyophilization. This is achieved by vacuum drying at a temperature below the equilibrium freezing point of the composition at which point the solvent (such as water) changes phase.

SUMMARY OF THE INVENTION

The term "fast-dispersing dosage form", as used herein and in the claims, refers to compositions which disintegrate/disperse within 1 to 60 seconds, preferably 1 to 30 seconds, more preferably 1 to 10 seconds and particularly 2 to 8 seconds, of being placed in the oral cavity. It therefore encompasses all the types of dosage forms described in the preceding paragraphs as well as any other equivalent dosage form. However, it is particularly preferred that the fast-dispersing dosage form is of the type described in U.K. Patent No. 1548022, that is, a solid fast-dispersing dosage form comprising a network of the active ingredient and a water-soluble or water-dispersible carrier which is inert towards the active ingredient, the network having been obtained by subliming solvent from a composition in the solid state, that composition comprising the active ingredient and a solution of the carrier in a solvent.

In the case of the preferred type of fast-dispersing dosage form described above, the composition will preferably contain, in addition to the active ingredient, matrix forming agents and secondary components. Matrix forming agents suitable for use in the present invention include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes.

Other matrix forming agents suitable for use in the present invention include sugars such as mannitol, dextrose, lactose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalarnine.

One or more matrix forming agents may be incorporated into the solution or suspension prior to solidification. The matrix forming agent may be present in addition to a surfactant or to the exclusion of a surfactant. In addition to forming the matrix, the matrix forming agent may aid in maintaining the dispersion of any active ingredient within the solution or suspension. This is especially helpful in the case of active agents that are not sufficiently soluble in water and must, therefore, be suspended rather than dissolved.

Secondary components such as preservatives, antioxidants, surfactants, viscosity enhancers, coloring agents, flavoring agents, pH modifiers, sweeteners or taste-masking agents may also be incorporated into the composition. Suitable coloring agents include red, black and yellow iron oxides and FD&C dyes such as FD&C Blue No. 2 and FD&C Red No. 40 available from Ellis & Everard. Suitable flavoring agents include mint, raspberry, licorice, orange, lemon, grapefruit, caramel, vanilla, cherry and grape flavors and combinations of these. Suitable pH modifiers include citric acid, tartaric acid, phosphoric acid, hydrochloric acid, maleic acid and sodium hydroxide. Suitable sweeteners include aspartame, acesulfame K and thaumatic. Suitable taste-masking agents include sodium bicarbonate, ion-exchange resins, cyclodextrin inclusion compounds, adsorbates or microencapsulated actives.

The compositions of the invention comprise an opioid ($\mu$ receptor) agonist as an active ingredient. Representative drugs within this class include, but are not limited to, alfentanil, codeine, diamorphine, dihydrocodeine, fentanyl, hydromorphine, methadone, morphine, morphine-6-glucoronide, oxymorphine, pethidine, sufentanil and tramadol and salts of these compounds. Such drugs are commercially available and their routes of administration and dosage rates are reported in the literature.

Thus, there is disclosed a pharmaceutical composition for oral administration comprising a carrier and, as active ingredient, an opioid agonist characterized in that the composition is in the form of a fast dispersing dosage form designed to release the active ingredient rapidly in the oral cavity.

A preferred active ingredient for use in the invention is fentanyl or a salt thereof. If a salt is used, it is preferred that the salt is an acid-addition salt of fentanyl, especially the citrate salt. However, since it is known that the un-ionized form of fentanyl penetrates mucosal membranes better than the ionized form, the composition of the invention may be buffered to a suitable pH range typically 7 to 7.5 by addition of an acid or alkaline substance.

The active ingredient is generally present in the composition in an amount from 0.2 to 95%, normally 1 to 20%, by weight of the composition of dried dosage form. Generally the active ingredient is present in an amount from 0.1 to 200 mg, normally 0.2 to 20 mg per dose depending upon the particular drug.

When the active ingredient is fentanyl it is preferably incorporated in the composition in an amount of from 0.5 to 10% by weight of the dried dosage form.

According to another aspect of the invention there is provided a process for preparing a pharmaceutical composition as previously defined which comprises bringing a carrier into association with the active ingredient.

In a further aspect, the invention provides the use of a fast-dispersing dosage form designed to release active ingredient rapidly in the oral cavity to deliver an opioid ($\mu$ receptor) agonist, such as fentanyl, or a salt thereof. A method of administering an opioid ($\mu$ receptor) agonist, such as fentanyl, or a salt thereof to a patient which comprises introducing into the oral cavity of the patient a composition as previously defined is also provided.

The invention also provides, in another aspect, a composition as defined above for use as an analgesic. The composition is particularly useful for the treatment of chronic pain, especially in a patient already receiving opioid therapy. In this respect, it is envisaged that the composition of the invention could provide the possibility of more individual titration of dose when required when the pain is most severe, especially during the night.

It is estimated that about 29% of patients with cancer continue to experience moderate to severe pain despite analgesic therapy and this can occur as intermittent breakthrough pain, often due to increases in a patient's activity level. Attempts to counteract this type of pain by increasing the dose of long-acting formulations of analgesics often produce slow onset of analgesia and unwanted side-effects of sedation, constipation or nausea and vomiting. However, the composition of the invention provides a rapidly acting, potent analgesic which would reduce the pain for the required time and then wear off fairly quickly thereby minimizing the side-effects of the active ingredient. Accordingly, the invention also provides a composition for use in the treatment of breakthrough pain in a patient experiencing chronic pain.

The composition of the invention is easier and quicker to administer than any of the existing dosage forms of fentanyl and other opioid (μ receptor) agonists. Thus, it is also suitable for administration in situations where an anesthetic, sedative or anxiolytic effect is required and the patient is conscious. The invention therefore also provides a composition for use as an anesthetic premedication, for the induction of anesthesia, for use as a sedative and/or for the treatment of anxiety.

According to a further aspect of the invention there is also provided the use of a composition as defined above for the manufacture of a medicament for use as an analgesic, for the treatment of chronic pain and/or breakthrough pain, as an anesthetic premedication, for the induction of anesthesia, as a sedative and/or for the treatment of anxiety.

A method of treating pain, especially chronic pain or breakthrough pain, or anxiety is also provided which comprises introducing into the oral cavity of a patient a therapeutically effective amount of a composition as previously defined.

The invention also provides a method of inducing an anesthetic effect or a sedative effect in a patient which comprises introducing into the oral cavity of the patient a pre-determined amount of a composition as previously defined calculated to induce anesthesia or sedation respectively in the patient.

DETAILED DESCRIPTION OF THE INVENTION

This invention is further illustrated by the following Examples.

EXAMPLE 1

Preparation of a Fast-dispersing Dosage Form Containing Fentanyl Citrate (a) Preparation of Fentanyl 0.126% Dispersion Gelatin (765 g) and mannitol (540 g) were dispersed in a portion of purified water (16 kg) by mixing thoroughly in the bowl of a vacuum mixer. The mix was then heated to 40° C.±2° C. and homogenised for ten minutes to allow complete dissolution of the solids. The mix was cooled down to room temperature (20–24° C.). When cooled, the fentanyl citrate (22.68 g), the aspartame (90 g), and mint flavour (90 g) were added sequentially to the mix. The mix was then homogenized to ensure complete dissolution of the solids. The remaining water (492 g) was added to the mixer and the bulk mix homogenized to ensure dissolution was complete.

(b) Preparation of Fentanyl 0.2 mg (as the Base) Units.

250 mg of fentanyl 0.126% dispersion formed in (a) above was dosed into each of one of a series of pre-formed blister pockets having a pocket diameter of about 12 mm. The blister laminate comprised 200 μm PVC (polyvinyl chloride) coated with 40 gsm PVdC (polyvinyl dichloride). The product was frozen immediately in a liquid nitrogen freeze tunnel. The frozen product was then stored below −20° C. for a minimum of 12 hours prior to freeze-drying in a freeze drier using a drying temperature of +10° C. and a chamber pressure of 0.5 mbar. The freeze dried units were then inspected for the presence of critical defects and the remainder of the batch sealed with lidding foil consisting of a paper/foil laminate (20 μm aluminium).

Each blister was then coded with a batch number and overwrapped in a preformed sachet by placing the blister in the sachet and sealing the open end of the sachet completely. Each sachet was then labelled with the product name, batch number, date of manufacture and suppliers name.

| Ingredient | Weight | % by Weight of Composition |
|---|---|---|
| Purified water EP/USP* | 229.061 | 91.624 |
| Fentanyl citrate EP/USP | 0.314 | 0.126 |
| Gelatin EP/USNF | 10.625 | 4.250 |
| Mannitol EP/USP | 7.500 | 3.000 |
| Mint Flavor | 1.250 | 0.500 |
| Aspartame EP/USNF | 1.250 | 0.500 |
| TOTAL | 250.000 | 100.000 |

*Ingredient removed during the lyophilization process.

EXAMPLES 2 TO 4

The following formulations were prepared by analogous methods to Example 1.

EXAMPLE 2

| Ingredient | Weight | % by Weight of Composition |
|---|---|---|
| Purified water EP/USP* | 227.497 | 90.999 |
| Fentanyl citrate EP/USP | 0.628 | 0.251 |
| Gelatin EP/USNF | 10.000 | 4.000 |
| Mannitol EP/USP | 7.500 | 3.000 |
| Citric Acid EP/USP | 1.250 | 0.500 |
| Glycine USP | 1.250 | 0.500 |
| Cherry Flavor | 1.875 | 0.750 |
| TOTAL | 250.000 | 100.000 |

*Ingredient removed during the lyophilization process.

EXAMPLE 3

| Ingredient | Weight | % by Weight of Composition |
|---|---|---|
| Purified water EP/USP* | 448.743 | 89.749 |
| Fentanyl citrate EP/USP | 1.257 | 0.251 |
| Gelatin EP/USNF | 22.500 | 4.500 |
| Mannitol EP/USP | 17.500 | 3.500 |
| Aniseed Flavor | 5.000 | 1.000 |
| Aspartame EP/USNF | 5.000 | 1.000 |
| TOTAL | 500.000 | 100.000 |

*Ingredient removed during the lyophilization process.

EXAMPLE 4

| Ingredient | Weight | % by Weight of Composition |
|---|---|---|
| Purified water EP/USP* | 457.169 | 91.434 |
| Fentanyl citrate EP/USP | 1.571 | 0.314 |
| Gelatin EP/USNF | 20.000 | 4.000 |
| Mannitol EP/USP | 15.000 | 3.000 |
| Grape Flavor | 2.500 | 0.500 |
| Aspartame EP/USNF | 3.750 | 0.750 |
| FD&C Blue No. 2 | 0.010 | 0.002 |
| TOTAL | 500.000 | 100.000 |

*Ingredient removed during the lyophilization process.

Examples 1 to 4 using fentanyl citrate correspond to 200, 400, 800 and 1000 µg of fentanyl base respectively.

Industrial Applicability

A need exists in the medical community for improved pain management. The present invention provides a dosage form that can be efficiently and economically used by patients for the management of their breakthrough pain. This is benefit to the patients and to the caregivers.

While the invention has been described through the use of specific embodiments, one skilled in the art will appreciate that various changes and modifications can be made without departing from the spirit and scope of the invention claimed herein.

What is claimed is:

1. A pharmaceutical composition for oral administration comprising a carrier and, as an active ingredient, an opioid agonist characterized in that said composition is in the form of a solid fast-dispersing dosage form comprising a network of said active ingredient and a water-soluble or water-dispersible carrier which is inert towards said active ingredient and wherein, said dosage form disintegrates within 1–30 seconds of being placed in the oral cavity.

2. The pharmaceutical composition of claim 1 in which the opioid agonist is fentanyl or a salt thereof.

3. The pharmaceutical composition of claim 1 wherein said network has been obtained by subliming solvent from a composition in the solid state, that composition comprising said active ingredient and a solution of the carrier in a solvent.

4. The pharmaceutical composition of claim 1 in which said active ingredient is present in an amount from 0.2 to 95% by weight of the composition.

5. The pharmaceutical composition of claim 2 which fentanyl or a salt thereof is present in an amount from 0.5 to 10% by weight of the composition.

6. The pharmaceutical composition of claim 2 in which the active ingredient is present in an amount from 0.1 to 200 mg per dosage form.

7. A method of providing anesthetic pre-medication, said method comprising the step of providing to a patient in need thereof the pharmaceutical composition according to claim 1.

8. A method of inducing anesthesia, said method comprising the step of administering a pharmaceutical composition according to claim 1 to a patient in need thereof.

9. A method of administering an opioid agonist to a patient which comprises introducing into the oral cavity of the patient a composition according to claim 1.

10. A method of treating pain which comprises introducing into the oral cavity of a patient a therapeutically effective amount of a composition according to claim 1.

11. The method according to claim 10 in which the pain is chronic pain.

12. The method according to claim 10 in which the patient is experiencing chronic and the pain to be treated is breakthrough pain.

* * * * *